United States Patent [19]

Anderson et al.

[11] Patent Number: 5,583,148
[45] Date of Patent: Dec. 10, 1996

[54] BIS-ACYLOXYMETHYL DERIVATIVES

[75] Inventors: Wayne K. Anderson, Williamsville, N.Y.; Dennis C. Dean, Iselin, N.J.

[73] Assignee: Research Foundation Of State University Of New York, Albany, N.Y.

[21] Appl. No.: 729,986

[22] Filed: Jul. 15, 1991

Related U.S. Application Data

[63] Continuation-in-part of Ser. No. 371,504, Jun. 26, 1989, abandoned.

[51] Int. Cl.$^6$ ............... C07D 219/08; C07D 217/10; C07D 215/10; A61K 31/435
[52] U.S. Cl. ............... 514/339; 514/297; 514/307; 514/314; 546/104; 546/143; 546/151; 546/156; 546/159; 546/279.1; 546/276.4; 546/276.7; 548/518; 548/561
[58] Field of Search ............... 546/104, 143, 546/151, 156, 159, 283, 272; 548/518, 561; 514/297, 307, 314

[56] References Cited

U.S. PATENT DOCUMENTS

| | | | |
|---|---|---|---|
| 4,529,728 | 7/1985 | Fabre | 546/272 |
| 4,539,400 | 9/1985 | Fabre | 546/272 |
| 4,684,658 | 8/1987 | Fabre | 546/246 |

OTHER PUBLICATIONS

Moossa et al "Oncology" William & Wilkins, p. 199 (1986).
DeVita "Cancer Principle and Practice of Oncology" Lippincott, p. 144–145 (1985).
Pazden et al "Correlation of Murine Anti tumor Models in Predicting Clinical Drug Activity in Nonsuall Cell by Cancer" Proc. Am. Soc. Clin. Oncology 3 p. 219 (1984).
Heim et al "L–Aspanaginase in the Treatment of Solid Tumor" Chem. Pharm. Abst. from Dtsch. Med. Wochschr. 95:989–93 (May 1, 1970).
Boyd et al "Basic Medical Microbiology" Brown & Co. pp. 117–139 (1977) Martin et al "Role of Marine Tumor Model" Cancer Re. 462189–92 (1986).

*Primary Examiner*—Ceila Chang
*Attorney, Agent, or Firm*—Crossetta & Associates

[57] ABSTRACT

This invention relates to new pyridyl, quinoline and acridine bis-acyloxymethyl compounds; to compositions comprising these compounds; and to processes for their utility as fungicides, bactericides and as inhibitors of the growth of cancer in warm-blooded animals. In accordance with this invention, new bis-acyloxymethyl derivatives are provided of the formula:

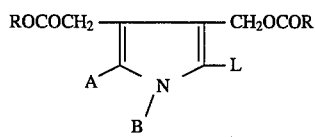

wherein B is selected from substituted and unsubstituted alkyl, cycloalkyl, aryl, alkenyl, cycloalkenyl and alkynyl; A is selected from hydrogen and B; or, A and B together comprise a pyrrolizine; L is selected from

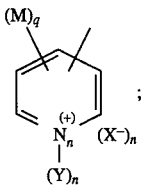

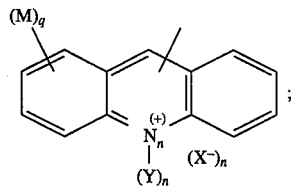

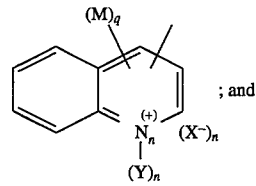

; and

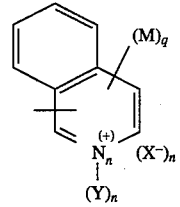

wherein Y is selected from hydrogen or

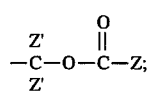

each R and Z is independently selected from hydrogen or substituted and unsubstituted alkyl, cycloalkyl, aryl, alkenyl, cycloalkenyl, alkynyl, amine group, each Z' is independently selected from hydrogen and substituted or unsubstituted alkyl; M is Z or is selected from halogen, nitro, hydroxyl, nitrile and substituted or unsubstituted, carboxylic acid group, carboxylic acid ester group, carboxylic acid amide group, sulfonic acid group and sulfonic acid amide group; ether group, thioether group, acylated hydroxyl, sulfonylamide, sulfonylurea, sulfoxide group, sulfone group and mixtures thereof; each n is the same and is 0 or 1; q is from 0–4; and, X is the anion of an acid.

23 Claims, No Drawings

BIS-ACYLOXYMETHYL DERIVATIVES

This application is a continuation-in-part of U.S. patent application Ser. No. 07/371,504, filed Jun. 26, 1989, now abandoned.

FIELD OF THE INVENTION

This application relates to new chemical compounds and to methods for their use as bactericides, fungicides and as compounds effective in inhibiting the growth of cancer tumors, particularly solid cancer tumors.

BACKGROUND OF THE INVENTION

There has been a continuing need for new and more effective chemical agents useful in the treatment of cancers in warm blooded animals, especially in human beings. Indeed, the concentrated effort of the National Cancer Institute over the last several years of their increased government funding has identified many new chemical compounds having efficacy in the inhibition of cancers in warm blooded animals, but which for a multiple of reasons, have not been commercially used in human cancer clinical treatment. Thus, the search for new compounds and pharmaceutical compositions continues.

One object of this invention is to provide new compounds and methods which are useful for inhibiting the growth of cancer.

Another object of this invention is to provide new pharmaceutical compositions which have utility in inhibiting the growth of cancer.

A still further object of this invention is to provide compounds having utility as bactericides or fungicides.

DESCRIPTION OF THE INVENTION

This invention relates to new bis-acyloxymethyl pyridyl, quinoline and acridine derivatives; to compositions comprising these compounds and to processes for their utility as fungicides, bactericides and as inhibitors of the growth of cancer, particularly solid tumor cancer, in warm blooded animals.

In accordance with this invention, new bis-acyloxymethyl derivatives are provided of the formula:

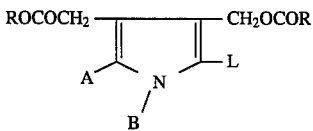

wherein B is selected from substituted and unsubstituted alkyl, cycloalkyl, aryl, alkenyl, cycloalkenyl and alkynyl; A is selected from hydrogen and B; or, A and B together comprise a pyrrolizine; L is selected from

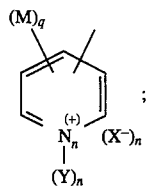

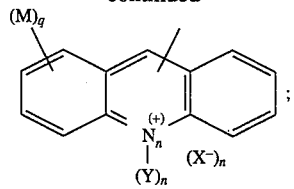

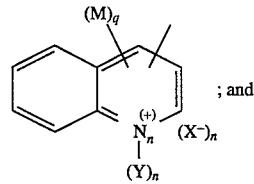

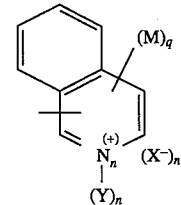

wherein Y is selected from hydrogen or

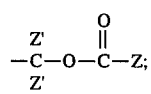

each R and Z is independently selected from hydrogen or substituted and unsubstituted alkyl, cycloalkyl, aryl, alkenyl, cycloalkenyl, alkynyl, amine group, each Z' is independently selected from hydrogen and substituted or unsubstituted alkyl; M is Z or is selected from halogen, nitro, hydroxyl, nitrile and substituted or unsubstituted, carboxylic acid group, carboxylic acid ester group, carboxylic acid amide group, sulfonic acid group and sulfonic acid amide group; ether group, thioether group, acylated hydroxyl, sulfonylamide, sulfonylurea, sulfoxide group, sulfone group and mixtures thereof; each n is the same and is 0 or 1; q is from 0–4; and, X is the anion of an acid.

Further in accord with the invention, new pharmaceutical compositions are provided which contain the compounds of the invention together with a pharmaceutical diluent.

Still further, in addition, a method of the invention is provided where one or more of the afore-described compounds is administered to fungi or bacteria in an amount sufficient to inhibit the growth thereof.

In another method of the invention, one or more of the afore-described compounds is administered to a cancer, particularly solid tumor cancer, containing warm blooded animal in an amount sufficient to inhibit the growth of said cancer.

Within the description of the compounds of the invention, particularly the designations A, B, R, M, X, Z, and Z', the terminology means as follows.

By the term alkyl, alkenyl and alkynyl is meant alkyl, alkenyl and alkynyl hydrocarbon substituents having from 1 to about 20 carbon atoms and preferably from 1 to about 12 carbon atoms. Such substituents can be straight chained or branched and include isomers thereof. Thus, the term alkyl includes methyl, ethyl, n-propyl, i-propyl, n-butyl, t-butyl, i-butyl, pentyl, hexyl, heptyl and the like up to about 20 carbon atoms. Similarly the terms alkenyl and alkynyl include unsaturated hydrocarbons having one or more double and triple bonds therein such as ethene, propene, butene, ethyne and the like up to about 20 carbon atoms and preferably from 1 to about 12 carbon atoms. By the terms cycloalkyl and cycloalkenyl is meant the alicyclic saturated and unsaturated hydrocarbons containing up to about 20 carbon atoms and preferably from 1 to about 12 carbon atoms, such as cyclopropyl, methylcyclopropyl, cyclobutyl, ethenylcyclobutyl, ethylcyclobutyl, cyclopentyl, cyclohexyl and the like.

By the term aryl, is meant cyclic aromatic and heteroaromatic structures which include benzene, naphthalene, pyridine, pyrimidine, quinoline, thiophene, indole, phenanthrene, anthracene, etc., up to a total of about 20 carbon atoms. The preferred aryl substituents are phenyl and napthyl.

By the term amine group is meant structures of the formula

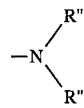

where R" is independently hydrogen or R', and R' substituted or unsubstituted alkyl, alkenyl, cycloalkyl, cycloalkenyl and aryl as previously described.

By the term nitrile is meant cyano or alkyl cyanides of the general formula C≡N.

By the term carboxylic acid group is meant an acid of the general structure:

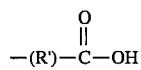

wherein R' is substituted or unsubstituted alkyl, alkenyl, cycloalkyl, cycloalkenyl and aryl as previously described, or, R' can additionally be a covalent bond. Such acids particularly include formic, acetic, propionic, butyric, valeric and the like carboxylic acids up to about 20 carbon atoms.

By the term carboxylic acid ester group is meant an ester which can be derived through a carboxylic acid and generally includes compounds of the structure:

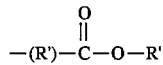

wherein R' is selected from substituted and unsubstituted alkyl, aryl, alkenyl, cycloalkyl and cycloalkenyl as previously described up to a total of about 20 carbon atoms. Generally, such ester can comprise straight hydrocarbon chains or branches and include the isomers thereof. Attachment can, of course, occur through the R' group or directly to the carbonyl by loss of R' group substituents. Typical examples include:

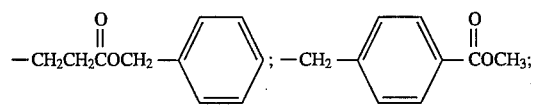

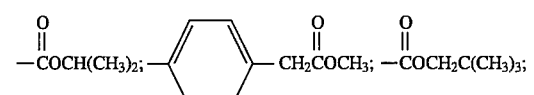

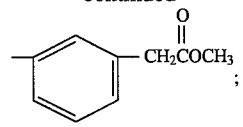

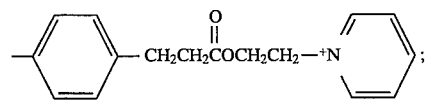

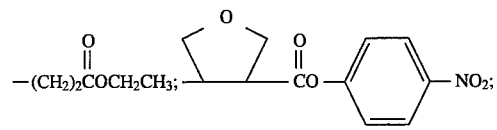

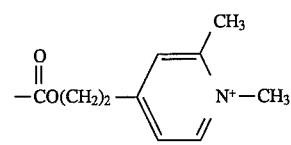

and the like.

By the term carboxylic acid amide group, is meant a compound having a general formula —(R')CONH$_2$, —(R')COHNR' or —(R')CONR'$_2$, wherein R' is substituted and unsubstituted as previously described up to about 20 carbon atoms and R' can additionally be a covalent bond. Typically, such amides can comprise straight hydrocarbon chains or branches and include the isomers thereof. Examples include:

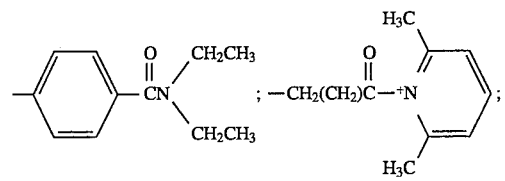

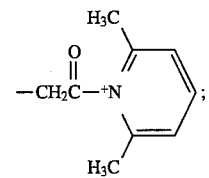

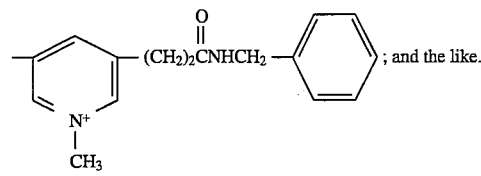

By the term ether group and thioether group is meant compounds of the general formula —(R')—O—R' and —(R')—S—R' wherein R' is substituted or unsubstituted as previously described up to about 20 carbon atoms. Generally, such ethers can comprise straight hydrocarbon chains or branches and include the isomers thereof. Thioether compounds are usually formed by the reaction of a thiol with an alkyl halide.

By the term sulfoxide group, sulfone group, sulfonylamide, and sulfonylurea is meant compounds of the formula:

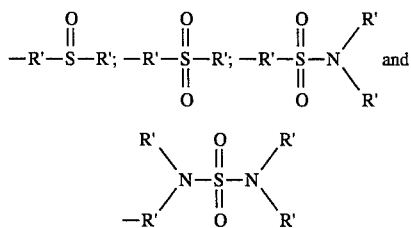

wherein R' is substituted or unsubstituted as previously described up to about 20 carbon atoms. Such compounds can comprise straight hydrocarbon chains, branches or isomers thereof. Sulfoxides are usually made by oxidation of a corresponding sulfide with reagents such as nitric acid, chromium trioxide or hydrogen peroxide, and the corresponding sulfone is prepared by further oxidizing the sulfoxides with hydrogen peroxide or potassium permanganate.

Appropriate substituents meant to be included for substitution on the substituted R, Z, Z' and M moieties of the invention are alkyl, cycloalkyl, aryl, alkenyl, cycloalkenyl, alkynyl, haloalkyl, amine group, alkylamino, alkenylamino, cycloalkylamino, arylamino, aminoalkyl, aminoalkenyl, aminocycloalkyl, aminocycloalkenyl, aminoaryl, carboxylic acid group, halogen, nitro, nitrile, carboxylic acid ester group, carboxylic acid amide group, ether group, thioether group, hydroxyl, acylated hydroxyl, sulfonylamide, sulfonylurea, sulfoxide group, sulfone group and mixtures thereof as before defined.

By the terms alkylamino, alkenylamino, cycloalkylamino and arylamino is meant compounds of the formula —NR"$_2$ and by the terms aminoalkyl, aminoalkenyl, aminocycloalkyl, aminocycloalkenyl and aminoaryl is meant compounds of the formula —R"NR"$_2$ wherein R" is selected from hydrogen or R', wherein R' is substituted and unsubstituted alkyl, alkenyl, cycloalkyl, cycloalkenyl and aryl having up to about 20 total carbon atoms; provided at least one R', in each formula, is not hydrogen.

By the terminology A and B together comprise a pyrrolizine is meant that A and B are cyclized with the carbon and nitrogen of the base structure to form a pyrrolizine base structure to which the acyloxymethyl moieties are appended. The term pyrrolizine base structure is meant to comprise a wide variety of pyrrolizine type structures including pyrrolizines, dihydropyrrolizines, benz-fused pyrrolizines, pyrroloquinolines, pyrroloisoquinolines, and the like.

By the term anion of an acid is meant the anion of any acid capable of forming an acid salt with the base structure. Particularly preferred are the halogens, e.g. iodine, chlorine and bromine. Generally, a strong mineral acid such as HCl, H$_2$SO$_4$ and the like is convenient in the manufacture of the acid salt, but generally, any acid, including acetic acid, the sulfonic acids and many of the carboxylic acids will readily form an acid salt with the base structure compounds of the invention. The bonding of the pyridine moiety to the pyrrolizine base structure can be through either an ortho, meta or para carbon to the pyridine ring nitrogen. Similarly, the M substituent can be bonded to any available carbon atom of the pyridine moiety. When n is 0 in this structure, the pyridine nitrogen is trivalent and does not contain the substituents or an ionic charge in the structure. When n is 1, the pyridine nitrogen is tetravalent, the nitrogen is substituted and has a positive charge for ionic bonding with X.

Typically, the preparation of the compounds of the invention can be attained through several routes. In one route, synthesis of the compounds of the invention can be conveniently achieved by first preparing the appropriate R and M substituted pyridyl, quinoline or acridine derivative. The R and M substituted derivative is then used to acylate the amino acid to form the appropriate amido acid, which is cyclized, reduced and transformed to the desired Y unsubstituted compound. Alkylating the pyridinium nitrogen to form the desired Y substituted acid salt compound typically comprises the final step.

Thus, for example, an appropriately substituted nicotinoyl or isonicotinyl chloride, prepared from the corresponding carboxylic acid, is reacted with 1-proline to give the α-amidoacid:

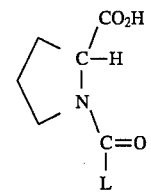

In further example, said appropriately substituted nicotinoyl or isonicotinyl chloride is reacted with an appropriately A and B substituted α-amino acid to give the α-amido acid as follows:

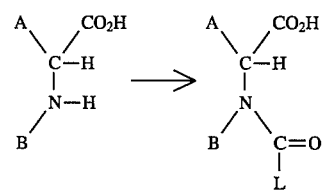

The α-amidoacids can then be transformed into the dimethyl 2,3-dihydro (2,3,4 or 5)-pyridinyl-1H-pyrrolizine-6,7-dicarboxylate or the dimethyl (2,3,4 or 5)-pyridinyl A and B substituted pyrrol-3,4-dicarboxylate by treatment with dimethyl acetylenedicarboxylate in acetic anhydride. The diesters are easily reduced to the diols with lithium aluminum hydride. The diols may be conveniently converted to bis-carbamates by treatment with an appropriate isocyanate and a catalytic amount of di(n-butyl)tin diacetate. Alkylation of the resulting pyridinyl-bis-carbamate with an appropriate selected α-acyloxymethyl iodide provides the appropriate Y substituted acyloxymethyl substituent of the base formula.

The medium on or within which the compounds of the invention can be used may be any solid or liquid. Examples of medium upon which the compounds may be used are organic tissue, surfaces, floors, walls, hardware, implements in general, paints textiles, leather, synthetic resins, foods, medicines, and other like substances. The compounds may be used in or on the medium as antiseptics, disinfectants, antimicrobial medicines or preservatives. They also may be used as additives to soaps, deodorants, and sterilizing solutions to enhance or provide antimicrobial properties to such products. A compound of the invention may be used alone, in mixture with other compounds of the invention, in mixture with other inhibiting compounds, with diluents, extenders, and carriers or the like. It is to be understood that concentrations of the compounds appropriate to be in actual contact with the microorganism vary widely and substantially higher concentrations may be appropriate in preparations where penetration through a substance is required in order to contact the microorganism with the compounds of the invention. A sufficient time to inhibit the growth of the microorganism depends upon the extent of inhibition required. Generally, the microorganism is inhibited by the compounds in from about 10 seconds to 30 minutes.

Microorganism as used herein includes any microorganism whose growth can be inhibited by the compositions of the invention. Such microorganisms can include almost all bacteria and also may include many fungi and perhaps even some viruses.

As previously discussed, another method of the invention comprises the chemical inhibition of the growth of cancerous tumor cells. In accordance with this method, an organism containing tumor cells is administered an effective tumor inhibiting concentration of a pharmaceutical composition comprising at least one compound of the invention preferably in acid salt form.

The quantity of the compound sufficient for treatment of cancer tumors varies depending upon the size of the warm blooded animal involved, upon the type of tumor and upon the species of the animal involved. In general, for most applications, the effective tumor inhibiting concentration of the compound of the invention usually ranges between about 0.5 and 1500 milligrams per kilogram of body weight of the organism being treated. The preferred concentration is between about 2 and about 400 milligrams per kilogram of body weight of the organism being treated. In general, large animals require less of any pharmaceutical compound per kilogram of body weight than smaller animals.

The method of the invention has numerous advantages over prior treatment methods which will become clear from the specification as set forth below. The compounds of the invention have a broad range of activity against multiple tumors over a broad range of doses. This makes the drug much more suitable for widespread use against different types of tumors and lowers the risk of toxic dose.

As used herein the term leukemic cancer refers to all cancers or neoplasms of the hemopoietic and immune systems (blood and lymphatic system). The term solid tumor as used herein are those epithelial neoplasms, such as skin and stomach cancer; connective tissue neoplasms, such as bone and smooth muscle cancer; neoplasms of the nervous system; neoplasms of multiple tissues, such as breast cancer and kidney cancer; and miscellaneous neoplasms such as ovarian cancer. Of particular interest is the activity of the compounds herein on the solid cancer tumors of the colon, lung, and breast.

The solid tumors are believed more difficult to treat than leukemic cancers as they are slower growing and denser. It is believed that most treatment materials are effective at the time of cell division. The slower growth means fewer cell divisions. The dense mass of tumor does not allow as ready access of the treatment compound to the tumor as the more widely separated cells of the leukemic blood cancers. Therefore, the activity of the compounds of the invention against solid tumors is unusual and of interest for solid tumor treatment.

Any suitable dosage may be given in the method of the invention. The type of and the amount of dosage will vary widely depending on the species of the warm blooded animal, body weight, and tumor being treated. Generally, a dosage of between about 2 milligrams per kilogram of body weight and about 400 milligrams per kilogram of body weight is suitable. Generally, the dosage per kilogram in man is lower than for small warm blooded mammals.

The pharmaceutical compositions of the invention may comprise a single compound of the invention or mixtures thereof with other compounds of the invention or other cancer inhibiting compounds. Pharmaceutical compositions can be in the form of a dosage unit and can also comprise diluents, extenders, carriers, and the like. The unit may be in solid or gel form such as pills, tablets, capsules, and the like or in liquid form suitable for oral, rectal, topical, or parenteral administration.

The method of treatment may be any suitable method which is effective in treatment of the particular tumor which is under treatment. Treatment may be oral, rectal, topical, parenteral, and the like. The method of applying an effective amount also varies depending on the tumor being treated. It is believed that parenteral treatment by intravenous, subcutaneous, or intramuscular application, formulated with an appropriate carrier, additional cancer inhibiting compound(s) or diluent to facilitate application, will be the preferred method of administering the compounds of the invention in warm blooded animals.

The following examples are meant to illustrate the invention and are not to be viewed as a limitation thereof. All temperatures are in degrees Centigrade unless otherwise denoted.

EXAMPLE I

2-Fluoropyridine-4-carbonyl chloride

Sodium nitrite (160 g, 2.32 mol) was gradually added in small portions, so that the reaction temperature never exceeded 10° C., to a mechanically stirred, ice-salt cooled solution of 2-amino-4-methylpyridine (250 g, 2.31 mol) in 48% fluoroboric acid (808 mL) and water (161 mL) contained in a 2 L three-necked round bottom flask. The solution was stirred at ice-salt bath temperature for 30 min. following the addition and then at 45° C. for 30 min. The solution was cooled to 0° C., neutralized to pH 7 with sodium carbonate and thereafter steam distilled. The pale yellow oil that separated from the distillate was removed and the remaining water layer was extracted with ether. The combined oil and ether extract was dried with sodium sulfate and concentrated in vacuo. The residue was distilled and gave 141 grams of 2-fluoro-4-methylpyridine having a boiling point of 63°–64° C.

A stirred mixture of 30 grams of the above 2-fluoro-4-methylpyridine and potassium permanganate (100 g) in water (1.2 L) was heated at reflux. Additional potassium permanganate (50 g) was added after 1.5 hours and the stirred mixture was maintained at reflux for 15 hours. The reaction mixture was then steam distilled to remove unreacted starting material, the hot residual aqueous solution was filtered, and the filtrate was concentrated in vacuo to 450 mL. The solution was cooled on an ice-bath and acidified with concentrated HCl to pH 2.0. The resulting precipitate was collected and crystallized from water and gave 13.56 g of 2-fluoropyridine-4-carboxylic acid having a melting point of 220°–224° C.

A mixture of the above 2-fluoropyridine-4-carboxylic acid (10 g) and thionyl chloride (70 mL) was heated at reflux for 25 hours. The excess thionyl chloride was removed by distillation at atmospheric pressure and the residue was distilled giving 9.51 grams of 2-fluoropyridine-4-carbonyl chloride having a boiling point of 88° C.

EXAMPLE II

2-Chloropyridine-4-carbonyl chloride

A mixture of pyridine-4-carboxylic acid-N-oxide (28 g) and phosphorous oxychloride (120 g) was heated at reflux for 7 hours. The reaction mixture was cooled and poured into ice-water (500 mL). The precipitate was collected and crystallized from a large volume of ethyl acetate and gave 23.1 grams of 2-chloropyridine-4-carboxylic acid as a white granular solid having a melting point of 225°–227° C.

A solution of 2-chloropyridine-4-carboxylic acid (10 g) in thionyl chloride (90 mL) was heated under reflux for 20 hours. The excess thionyl chloride was removed by distillation at atmospheric pressure and the oily residue was distilled to give 9.26 grams of 2-chloropyridine-4-carbonyl chloride having a boiling point of 144°–148° C.

EXAMPLE III

N-(2-Fluoropyridine-4-carboxy)-1-Proline

A solution of 2-fluoropyridine-4-carbonyl chloride (9.51 g) in anhydrous acetone (35 mL) was added dropwise, with simultaneous addition of 2N sodium hydroxide to maintain the reaction mixture at pH 8–9, to a stirred solution of l-proline (8.85 g) in 2N sodium hydroxide (38.9 mL), 1N sodium bicarbonate (56 mL) and acetone (70 mL) at 0° C. and then at room temperature for 1 hour. The reaction mixture was concentrated to one-third of the original volume in vacuo, cooled and acidified with concentrated HCl. The mixture was extracted with dichloromethane (3×250 mL). The combined organic phase was washed with saline (2×100 mL), dried with sodium sulfate and concentrated in vacuo. The oily residue was cooled and treated with n-hexane. The resulting solid was washed with n-hexane and crystallized from dichloromethane-n-hexane to give the titled product as a white granular solid (13.9 g) having a melting point of 120°–123° C.

In a similar manner, N-(2-Fluoropyridine-4-carboxy)-2-methylamino-2-phenylethanoic acid is prepared by adding a solution of 2-fluoropyridine-4-carbonyl chloride in anhydrous acetone, dropwise with simultaneous addition of 2N sodium hydroxide to maintain the reaction mixture at pH 8–9, to a stirred solution of 2-methylamino-2-phenylethanoic acid in 2N sodium hydroxide, 1N sodium bicarbonate and acetone at 0° C. and then at room temperature for 1 hour. The reaction mixture is concentrated to one-third of the original volume in vacuo, cooled and acidified with concentrated HCl. The mixture is extracted with dichloromethane and the combined organic phase is washed with saline, dried with sodium sulfate and concentrated in vacuo. The residue is cooled, treated with n-hexane and the resulting solid is washed and crystallized to give the N-(2-fluoropyridine-4-carboxy)-2-methylamino-2-phenylethanoic acid.

EXAMPLE IV

N-(2-Chloropyridine-4-carboxy)-1-proline

2-Chloropyridine-4-carbonyl chloride prepared in accord with Example II was treated with l-proline as described in Example III. The product was crystallized from dichloromethane-benzene to give the titled compound as a white granular solid having a melting point of 129°–131° C.

EXAMPLE V

Dimethyl 2,3-Dihydro-5-[4-(2-fluoropyridinyl)]-1H-pyrrolizine-6,7-dicarboxylate A stirred mixture of N-(2-fluoropyridine-4-carboxy)-(1)-proline (14.57 g), dimethyl acetylenedicarboxylate (26.08 g) and acetic anhydride (260 mL) was heated at 75° C. for 22 hours until carbon dioxide evolution had ceased. The volatiles were removed from the reaction mixture in vacuo (75° C.) and the oily residue was purified by flash chromatography (hexane-ethyl acetate, 1:1). The product was crystallized from methanol to give the titled compound as fine needles (11.6 g) having a melting point of 142°–143° C.

In a similar manner dimethyl 1-methyl-2-[4-(2-fluoropyridinyl)]-5-phenylpyrrole-3,4-dicarboxylate is prepared by heating a stirred mixture of N-(2-fluoropyridine-4-carboxy)-2-methylamino-2-phenylethanoic acid, dimethyl acetylenedicarboxylate and acetic anhydride, at 75° C. for 22 hours until carbon dioxide evolution ceases. The volatiles are removed from the reaction mixture in vacuo (75° C.) and the oily residue is purified by flash chromatography. The product is crystallized to give the dimethyl 1-methyl-2-[4-(2-fluoropyridinyl)]-5-phenylpyrrole-3,4-dicarboxylate.

EXAMPLE VI

Dimethyl 2,3,-Dihydro-5-[4-(2-chloropyridinyl)]-1H-pyrrolizine-6,7-dicarboxylate N-(2-Chloropyridine-4-carboxy)-(1)-proline was converted to the titled compound by the process described in Example V. The product was crystallized from methanol to give the titled compound as yellow plates having a melting point of 128°–130° C.

EXAMPLE VII

Dimethyl 2,3-Dihydro-5-(4-pyridinyl)-1H-pyrrolizine-6,7-dicarboxylate

Method A. Reduction with Zinc Acetic Acid. A mixture of the diester of the titled compound of Example V (1.16 g) and zinc powder (15 g) in glacial acetic acid (40 mL) was stirred at room temperature for 48 hours. Dichloromethane (200 mL) was added and the mixture was filtered. Saturated sodium carbonate solution was added to the filtrate until the aqueous phase was alkaline. The residue was crystallized from ethyl acetate-n-hexane to give 0.63 grams of the titled compound as colorless fine needles having a melting point of 180°–181° C.

In a similar manner dimethyl 1-Methyl-2-(4-pyridinyl)-5-phenylpyrrole-3,4-dicarboxylate is prepared by zinc acetic reduction by preparing a mixture of the dimethyl 1-methyl-2-[4-(2-fluoropyridinyl)]-5-phenylpyrrole-3,4-dicarboxylate of Example V and zinc powder in glacial acetic acid and stirring at room temperature for 48 hours. Dichloromethane is added and the mixture is filtered. Saturated sodium carbonate solution is added to the filtrate until the aqueous phase is alkaline. The residue is crystallized and comprises dimethyl 1-Methyl-2-(4-pyridinyl)-5-phenylpyrrole-3,4-dicarboxylate.

Method B. Catalytic Hydrogenolysis. A solution of the diester of the titled compound of Example V (2 g) in absolute ethanol (75 mL) was added to a suspension of 10% palladium on carbon (0.4 g) in 2N HCl (15 mL) in a hydrogenation bottle. The mixture was then hydrogenated for 10 hours at 35 psi hydrogen atmosphere with mechanical shaking. The mixture was filtered through a pad of celite and the ethanol was removed in vacuo. Sodium carbonate was added to the aqueous solution to make it basic (pH 9), and the solution was extracted with dichloromethane (3×150 mL). The organic solution was dried (sodium sulfate) and concentrated in vacuo. The slightly yellow white solid residue was subjected to flash chromatography (ethyl acetate) to give 1.345 grams of the titled compound, as a white solid. This compound was identical to that obtained using Method A.

In a similar manner a solution of dimethyl 1-methyl-2-[4-(2-fluoropyridinyl)]-5-phenylpyrrole-3,4-dicarboxylate of Example V, in absolute ethanol, is added to a suspension of 10% palladium on carbon in 2N HCl in a hydrogenation bottle. The mixture is then hydrogenated for 10 hours at 35 psi hydrogen atmosphere with mechanical shaking. The mixture is filtered through a pad of celite and the ethanol is removed in vacuo. Sodium carbonate is added to the aqueous solution to make it basic (pH 9), and the solution is extracted with dichloromethane. The organic solution is dried (sodium sulfate) and concentrated in vacuo. The residue is subjected to flash chromatography to give the dimethyl 1-Methyl-2-(4-pyridinyl)-5-phenylpyrrole-3,4-dicarboxylate, which is identical to that obtained using Method A.

EXAMPLE VIII 2,3-Dihydro-5-(4-pyridinyl)-6,7-bis(hydroxymethyl)-1H-pyrrolizine The diester of Example VII (2.0 g) was added portionwise to a stirred suspension of lithium aluminum hydride (0.632 g) in anhydrous tetrahydrofuran (50 mL) that was cooled to −15° C. (ethylene glycol-dry ice) and maintained under an argon atmosphere. The mixture was stirred for 2 hours at −15° C. The excess hydride was destroyed by the cautious addition of 5 percent sodium hydroxide solution (10 mL). Dichloromethane (200 mL) was added, the mixture was filtered and the inorganic precipitate was washed with hot dichloromethane (200 mL). The combined filtrate was washed with brine, dried with sodium sulfate and concentrated in vacuo. The solid residue was dried (over phosphorous pentoxide in vacuo) to give 1.6 grams of the titled compound 98% having a crude melting point of 173°–175° C.

In a similar manner, the dimethyl 1-Methyl-2-(4-pyridinyl)-5-phenylpyrrole-3,4-dicarboxylate diester of Example VII is added portionwise to a stirred suspension of lithium aluminum hydride in anhydrous tetrahydrofuran that is cooled to −15° C. (ethylene glycol-dry ice) and maintained under an argon atmosphere. The mixture is stirred for 2 hours at −15° C. The excess hydride is destroyed by the cautious addition of 5 percent sodium hydroxide solution. Dichloromethane is added, the mixture is filtered and the inorganic precipitate is washed with hot dichloromethane. The combined filtrate is washed with brine, dried with sodium sulfate and concentrated in vacuo. The solid residue is dried (over phosphorous pentoxide in vacuo) to give the 3,4-bis(Hydroxymethyl)-1-methyl-5-phenyl-2-(4-pyridinyl)pyrrole.

EXAMPLE IX 2,3-Dihydro-5-[4-(2-fluoropyridinyl)]-6,7-bis(hydroxymethyl)-1H-pyrrolizine The diester of Example V was reduced as described in Example VIII. The oily product was crystallized from dichloromethane-benzene to give the titled compound as white crystals having a melting point of 135°–139° C.

EXAMPLE X 2,3-Dihydro-5-[4-(2-chloropyridinyl)-6,7-bis(hydroxymethyl)-1H-pyrrolizine]

The diester of Example VI was reduced as described in Example VIII. The oily product was crystallized from dichloromethane-n-hexane to give the titled compound as pale yellow crystals having a melting point of 145°–149° C.

In a similar manner, a 2,6-dichloropyridinyl dicarboxylate analog of Example VI was reduced as described in Example VIII and crystalized from dichloromethane-n-hexane to give 2,3-dihydro-5-[-(2,6-dichloropyridinyl)-6,7-bis(hydroxymethyl)-1H-pyrrolizine] hereinafter referred to as the diol of Example Xa.

EXAMPLE XI 2,3-Dihydro-5-(4-pyridinyl)-6,7-bis(hydroxymethyl)-1H-pyrrolizine Bis[N-(2-propyl)carbamate]

A mixture of the titled diol compound of Example VIII (1.6 g), 2-propylisocyanate (1.23 g) and dibutyltin diacetate (2 drops) in anhydrous dichloromethane (50 mL) was stirred at room temperature under an argon atmosphere for 15 hours. The mixture was concentrated in vacuo and the residue was subjected to flash chromatography to give the titled carbamate compound as an amorphous white powder (0.66 g) having a melting point of 160°–162° C.

In a similar manner a mixture of the 3,4-Bis(Hydroxymethyl)-1-methyl-5-phenyl-2-(4-pyridinyl)pyrrole, as prepared in Example VIII, 2-propylisocyanate and dibutyltin diacetate (2 drops) in anhydrous dichloromethane are stirred at room temperature under an argon atmosphere for 15 hours. The mixture is concentrated in vacuo and the residue is subjected to flash chromatography to give the 3,4-bis(hydroxymethyl)-1-methyl-5-phenyl-2(4-pyridinyl)pyrrole Bis [N-(2-propyl)carbamate]. Reacting the carbamate with iodomethyl propionate in accord with Example III will provide the iodide salt.

EXAMPLE XII 2,3-Dihydro-5-[4-(2-fluoropyridinyl)]-6,7-bis(hydroxymethyl-1H-pyrrolizine Bis[N-(2-propyl)carbamate]

The diol of Example IX was acylated as described in Example XI. The product was crystallized from ethyl acetate to give the titled compound as an amorphous white powder having a melting point of 160°–162° C.

In a similar manner the diols of Examples X and Xa were acylated as described in Example XI and crystalized from isopropyl ether to give 2,3-Dihydro-5-[4-(2-chloropyridinyl)]-6,7-bis(hydroxymethyl-1H-pyrrolizine Bis[N-(2-propyl)carbamate], hereinafter referred to as Example XIIa, and 2,3-Dihydro-5-[4-(2,6-dichloropyridinyl)]-6,7-bis(hydroxymethyl-1H-pyrrolizine Bis[N-(2-propyl)carbamate], hereinafter referred to as Example XIIb, respectively.

EXAMPLE XIII

1-[(Propionyloxy)methyl]-4-{5-[2,3-dihydro-6,7-bis(n-(2-propyl)carbamoyloxyethyl)-1H-pyrrolizinyl} Pyridinium iodide The bis-carbamate of Example XI (0.35 g) was dissolved in anhydrous dichloromethane (7 mL) at room temperature. Iodomethyl propionate (0.36 g) was added and the mixture was stirred at room temperature under an argon atmosphere for 18 hours. Anhydrous ether (50 mL) was added and the mixture was stirred for 0.5 hours. The precipitate was collected, washed with anhydrous ether (100 mL) and re-precipitated from dichloromethane-ethyl ether to give 0.47 g of the titled compound as a yellow solid having a melting point of 163°–165° C.

EXAMPLE XIV

1-[(Benzoyloxy)methyl]-4-{5-[2,3-dihydro-6,7-bis(N-(2-propyl)carbamoyloxymethyl)-1H-pyrrolizinyl]} pyridinium iodide The bis-carbamate of Example XI (0.40 g) was dissolved in anhydrous dichloromethane (3 mL) at room temperature. Iodomethyl benzoate (0.85 g) was added and the mixture stirred at room temperature under an argon atmosphere for 36 hours. Anhydrous ether (50 mL) was added and the mixture was stirred for 0.5 hours. The precipitate was collected, washed with anhydrous ether (100 mL) and re-precipitated from dichloromethane-ethyl ether to give 0.56 grams of the titled compound as a yellow solid having a melting point of 183°–187° C.

EXAMPLE XV

2-Fluoropyridine-5-carbonyl chloride

2-Amino-5-methylpyridine (200 g) was dissolved in 40% fluoroboric acid (830 mL) and the temperature was lowered to −10° C. (ice-salt bath). Sodium nitrite (130 g) was added slowly, in small portions, so as not to allow the temperature to rise above 0° C. The reaction mixture was stirred at 0° C. for 0.5 hours and then warmed to 50° C. for 30 minutes. Sodium carbonate was added to make the solution alkaline (pH 8.0). The mixture was steam distilled until the distillate was no longer cloudy. The yellowish oil that separated from the water layer was removed and the water layer was extracted with ethyl ether (1 L). The ether extracts and oil layer were combined, dried (sodium sulfate), and the solvent was removed in vacuo. The remaining residue was distilled to give 2-fluoro-5-methylpyridine as a pale yellow oil (85.2 g) having a boiling point of 70°–74° C.

A solution of the 2-fluoro-5-methylpyridine (30 g) in water (1.2 L) was stirred with a mechanical stirrer, potassium permanganate (100 g) was added in portions and the mixture heated to 100° C. When the characteristic purple color of the mixture faded to black, another portion of potassium permanganate (50 g) was added and the mixture was then stirred at 100° C. for 4.5 hours. The mixture was filtered hot, the filtrate was cooled and extracted with ether to remove unreacted starting material. The aqueous layer was neutralized to pH 7 with concentrated HCl and concentrated to a volume of 350 mL. The pH was lowered by addition of concentrated HCl to pH 4–2 at which point a large amount of precipitate appeared. The precipitate was filtered and the aqueous layer was extracted with ethyl acetate (500 mL). The organic layer was dried, evaporated, and the solids combined to give 2-fluoropyridine-5-carboxylic acid (17.1 g) as a colorless solid having a melting point of 275°–278° C.

EXAMPLE XVI

2-Chloropyridine-5-carbonyl chloride

2-Chloropyridine-5-carboxylic acid (25 g) was dissolved in thionyl chloride (200 mL) and the mixture was heated at reflux for 24 hours. The excess thionyl chloride was removed by distillation at atmospheric pressure and the residue was distilled under reduced pressure to yield the titled compound as a clear oil (26.4 g) having a boiling point of 128°–130° C.

EXAMPLE XVII

N-(2.-Fluoropyridine-5-carboxy)-l-proline l-proline (9.28 g) was dissolved in distilled water (120 mL), acetone (60 mL) was added and the solution was cooled to ice-bath temperature. The pH was adjusted to 8–9 with 1N sodium hydroxide and a solution of the acid chloride of Example XV (10 g) in acetone (40 mL) was added dropwise. Sodium hydroxide solution (2N) was also added to keep the pH at 8–9 and the mixture was allowed to stir at room temperature for 15 hours. The mixture was extracted with ether (100 mL), acidified to pH 2 with concentrated HCl, and extracted with ethyl acetate (2×400 mL). The ethyl acetate layer was washed with water (2×150 mL), brine (150 mL), dried (sodium sulfate), and the solvent removed in vacuo to yield the titled compound as a hygroscopic pinkish oil (11.0 g).

EXAMPLE XVIII

N-(2-Chloropyridine-5-carboxy)-l-proline l-proline was acylated with the compound of Example XVI as described in Example XVII. The titled product was obtained as a hygroscopic colorless oil.

EXAMPLE XIX

Dimethyl-1,2-Dihydro-5-(2-fluoropyridin-5-yl)-1H-pyrrolizine-6,7-dicarboxylate)

A mixture of the compound of Example XVII (11 g), dimethyl acetylenedicarboxylate (9.84 g), and acetic anhydride (130 mL) was heated at 68° C. for 15 hours until evolution of carbon dioxide had ceased. The mixture was then heated to 80°–85° C. and excess acetic anhydride and dimethyl acetylenedicarboxylate was removed by distillation under reduced pressure. The residue was subjected to flash chromatography to give the titled compound as colorless crystals (10.5 g) having a melting point of 135°–138° C.

EXAMPLE XX

Dimethyl-1,2-dihydro-5-(3-pyridinyl)-1H-pyrrolizine-6,7-dicarboxylate

Method B, used for the synthesis in Example VII was used to reductively defluorinate the diester of Example XIX to give the titled compound (80%) as a white solid having a melting point of 180°–182° C.

EXAMPLE XXI

Dimethyl-1,2-dihydro-5-(2-chloropyridin-5-yl)-1H-pyrrolizine-6,7-dicarboxylate

The amido acid of Example XVIII was converted to the titled compound by the method described in Example XIX. The titled product had a melting point of 164°–166° C.

EXAMPLE XXII 2,3-Dihydro-5-(3-pyridinyl)-6,7-bis(hydroxymethyl)-1H-pyrrolizine Bis[N-(2-propyl)carbamate]

A solution of the diester of Example XX (3.5 g) in anhydrous tetrahydrofuran (45 mL) was added dropwise over a period of 30 minutes under an argon atmosphere to a suspension of lithium aluminum hydride (1.1 g) in anhydrous tetrahydrofuran (20 mL) and cooled to −15° C. The mixture was stirred for 2 hours at −15° C. and the reaction was carefully quenched with 5% sodium hydroxide (10 mL). Dichloromethane (250 mL) was added and the inorganic salts were filtered and washed with hot dichloromethane (300 mL). The organic layers were combined, dried with sodium sulfate and concentrated in vacuo to yield a light yellow solid which was resuspended in anhydrous dichloromethane (60 mL). Isopropyl isocyanate (2.15 g) and dibutyltin diacetate (5 drops) were added and the reaction mixture was stirred under an argon atmosphere for 24 hours. The mixture was concentrated in vacuo and the pale yellowish solid was subjected to flash chromatography (ethyl acetate) to give the titled compound as colorless needles (3.65 g) having a melting point of 156°–158° C.

EXAMPLE XXIII 2,3-Dihydro-5-[5-(2-fluoropyridinyl)]-6,7-bis(hydroxymethyl)-1H-pyrrolizine Bis[N-(2-propyl)carbamate]

The diester of Example XIX was reduced and the resulting diol was carbamoylated as described in Example XXII. The titled product (85%) colorless needles was recovered having a melting point of 178°–180° C.

EXAMPLE XXIV 2,3-Dihydro-5-[5-(2-chloropyridinyl)]-6,7-bis(hydroxymethyl)-1H-pyrrolizine Bis[N-(2-propyl)carbamate]

The diester of Example XXI was reduced and the resulting diol was carbamoylated as described in Example XXII. The crude product, a pale yellow solid, was subjected to flash chromatography (n-hexane-ethyl acetate, 1.5:1) to give the titled compound in the form of colorless needles having a melting point of 174°–176° C.

EXAMPLE XXV

1-[(Propionyloxy)methyl]-3-{5-[2,3,-dihydro-6,7-bis(N-(2-propyl)carbamoyloxymethyl)-1H-pyrrolizinyl]}pyridinium iodide The procedure used to prepare the compound of Example XIII was used to alkylate the bis-carbamate of Example XXII with iodomethyl propionate to give the titled product (73%) as a yellow solid having a melting point of 112°–117° C.

EXAMPLE XXVI

1-[(Benzoyloxy]methyl]-3-{5-[2,3-dihydro-6,7-bis(N-(2-propyl)carbamoyloxymethyl)-1H-pyrrolizinyl]}pyridinium iodide The procedure used to prepare the compound of Example XIV was used to alkylate the bis-carbamate of Example XXIII with iodomethyl benzoate to give the titled product as a yellow solid having a melting point of 120°–125° C.

EXAMPLE XXVII

1-Methyl-4-{5-[2,3-dihydro-6,7-bis(N-(2-propyl)carbamoyloxymethyl)-1H-pyrrolizinyl]}pyridinium iodide A solution of the product of Example XI (0.20 g) and iodomethane (2 mL) in anhydrous acetone (30 mL) was stirred at room temperature for 27 hours under an argon atmosphere. A yellow precipitate appeared. Anhydrous ether (100 mL) was added, the mixture was stirred for an additional 0.5 hour and filtered. The solid was washed with anhydrous ether (100 mL) and dried in vacuo over phosphorous pentoxide. Re-precipitation from anhydrous dichloromethane-ether gave the titled product as a yellow powder (0.25 g) having a melting point of 209°–211° C.

EXAMPLE XXVIII

1-Methyl-3-{5-[2,3-dihydro-6,7-bis(N-(2-propyl)carbamoyloxymethyl)-1H-pyrrolizinyl]}pyridinium iodide The biscarbamate of Example XXII was treated with iodomethane as described in Example XXVII to give the titled compound as a yellow powder (0.26 g) having a melting point of 187°–190° C.

EXAMPLE XXIX

P338 Leukemia activity, in vivo

Various of the compounds of the invention prepared in accord with Examples I–XXVIII, were tested for anti-tumor activity in vivo using the P338 leukemia test procedure in mice, with compounds adriamycin (ADM) and mitomycin (MMC) representing controls. The compounds of the invention, which were tested, are designated with the Example number corresponding to its preparation. The compound designated XIa is the 2',6'-dichloro analog of the compound of Example XI.

The test system was that employed by the National Cancer Institute (NCI) for the preliminary screening of anti-tumor agents, according to protocol 1.200 (Cancer Chemo. Reports Part 3, Vol. 3, No.2, page 9; 1972). In the study ascitic fluid containing approximately $1.0 \times 10^5$ cells was implanted into the peritoneal cavity of CDF1 female mice on day zero(0). The compounds of the invention were administered in saline, intraperitoneally in single injections in 4–7 different dose levels (4 mice/dose level) daily, beginning on day 1 for the number of doses indicated. The treated control animals received MMC (5 mice/dose level) and ADM (2 dose levels). Untreated control animals received no drugs. The test was run for 45 days or until the animal died, whichever occurred first. Test criteria was in accord with the NCI protocol. Toxicity Day Survivors (TDS), was evaluated on day 5 of the test and sets out the number of survivors/number of animals tested. Body Weight Difference (BWD)

was also evaluated on day 5 of the test and is determined by subtraction of the average control group body weight change from the average test group body weight change during the 5 day period. Life Span sets out the day of death of each test animal. A Life Span of 45 days indicates that the animal lived for the entire test period and is considered a "Cure" within the test protocol. Accordingly, "Cures" indicate a 45 day survival of the test animal. %T/C data was calculated through mean survival time of the test animals compared to the controls. Therefore %T/C represents the mean survival time of compound treated animals divided by the mean survival time of control animals, expressed as a percent. Table I comprises the results of the testing protocol.

TABLE I

P388 LEUKEMIA IN VIVO

| Compd | Dose (mg/kg) | No. of Doses | TDS | Life Span | BWD (T-C, grams) | % T/C (cures) |
|---|---|---|---|---|---|---|
| Example XIII | 200 | 2 | 0/4 | 02, 03, 03, 03 |  | 24 |
|  | 100 | 3 | 2/4 | 04, 04, 06, 10 | −5.7 | 51 |
|  | 50 | 5 | 4/4 | 10, 45, 45, 45 | −3.6 | 311 (3/4) |
|  | 25 | 5 | 4/4 | 45, 45, 45, 45 | −2.1 | 386 (4/4) |
|  | 12.5 | 5 | 4/4 | 23, 45, 45, 45 | −0.9 | 316 (3/4) |
|  | 6.2 | 5 | 4/4 | 18, 19, 45, 45, | −0.2 | 264 (2/4) |
|  | 3.1 | 5 | 4/4 | 18, 19, 21, 22 | −0.1 | 160 |
| Example XIV | 200 | 1 | 0/4 | 02, 02, 03, 03 |  | 21 |
|  | 100 | 4 | 3/4 | 03, 07, 07, 07 | −5.1 | 51 |
|  | 50 | 5 | 4/4 | 16, 45, 45, 45 | −3.4 | 324 (3/4) |
|  | 25 | 5 | 4/4 | 15, 28, 45, 45 | −1.5 | 285 (2/4) |
|  | 12.5 | 5 | 4/4 | 45, 45, 45, 45 | −0.3 | 360 (4/4) |
|  | 6.2 | 5 | 4/4 | 19, 21, 22, 35 | −0.5 | 194 |
|  | 3.1 | 5 | 4/4 | 12, 14, 18, 21 | 0.3 | 130 |
| Example XI | 100 | 4 | 4/4 | 07, 07, 08, 08 | −4.4 | 64 |
|  | 50 | 5 | 4/4 | 08, 09, 09, 09 | −4.1 | 75 |
|  | 25 | 5 | 4/4 | 08, 17, 21, 45 | −3.4 | 195 (1/4) |
|  | 12.5 | 5 | 4/4 | 16, 18, 18, 31 | 0 | 166 |
|  | 6.2 | 5 | 4/4 | 14, 16, 18, 18 | −0.2 | 132 |
|  | 3.1 | 5 | 4/4 | 14, 15, 16, 18 | −0.1 | 126 |
| Example XXV | 200 | 5 | 4/4 | 08, 21, 45, 45 | −3.8 | 255 (2/4) |
|  | 100 | 5 | 4/4 | 45, 45, 45, 45 | −2.0 | 386 (4/4) |
|  | 50 | 5 | 4/4 | 17, 18, 45, 45 | −1.0 | 268 (2/4) |
|  | 25 | 5 | 4/4 | 15, 16, 25, 45 | −1.1 | 216 (1/4) |
| Example XXVI | 200 | 5 | 4/4 | 05, 07, 07, 07 | −4.5 | 56 |
|  | 100 | 5 | 4/4 | 45, 45, 45, 45 | −4.0 | 386 (4/4) |
|  | 50 | 5 | 4/4 | 15, 28, 45, 45 | 0.1 | 285 (2/4) |
|  | 25 | 5 | 4/4 | 15, 28, 45, 45 | −0.6 | 285 (2/4) |
|  | 12.5 | 5 | 4/4 | 18, 22, 22, 26 | −0.3 | 176 |
|  | 6.2 | 5 | 4/4 | 13, 16, 16, 21 | −0.1 | 132 |
|  | 3.1 | 5 | 4/4 | 15, 16, 16, 21 | −0.1 | 136 |
| Example XXII | 200 | 2 | 3/4 | 02, 07, 07, 07 | −5.1 | 49 |
|  | 100 | 3 | 3/4 | 02, 08, 09, 09 | −5.0 | 60 |
|  | 50 | 5 | 4/4 | 10, 17, 18, 19 | −3.8 | 137 |
|  | 25 | 5 | 4/4 | 10, 14, 16, 21 | −2.6 | 131 |
|  | 12.5 | 5 | 4/4 | 11, 15, 16, 16 | −0.9 | 116 |
|  | 6.2 | 5 | 4/4 | 14, 15, 15, 16 | 0.3 | 120 |
| Example XXIb | 200 | 5 | 4/4 | 15, 16, 17, 18 | −1.9 | 141 |
|  | 100 | 5 | 4/4 | 14, 14, 14, 16 | −1.7 | 124 |
|  | 50 | 5 | 4/4 | 14, 14, 14, 16 | −0.5 | 124 |
|  | 25 | 5 | 4/4 | 13, 13, 14, 16 | −0.2 | 120 |
| Example XXIII | 200 | 5 | 4/4 | 05, 05, 05, 07 | −5.5 | 33 |
|  | 100 | 5 | 4/4 | 05, 05, 09, 10 | −5.0 | 62 |
|  | 50 | 5 | 4/4 | 04, 14, 18, 21 | −4.4 | 122 |
|  | 25 | 5 | 4/4 | 14, 15, 18, 18 | −3.5 | 164 |
|  | 12.5 | 5 | 4/4 | 15, 15, 15, 15 | −2.2 | 126 |
|  | 6.2 | 5 | 4/4 | 14, 15, 15, 16 | −0.8 | 120 |
| Example XII | 200 | 3 | 3/4 | 04, 05, 07, 07 | −5.0 | 49 |
|  | 100 | 4 | 4/4 | 05, 05, 09, 10 | −4.9 | 81 |
|  | 50 | 5 | 4/4 | 04, 14, 18, 21 | −4.0 | 208 |
|  | 25 | 5 | 4/4 | 14, 15, 18, 18 | −1.9 | 204 |
|  | 12.5 | 5 | 4/4 | 18, 18, 19, 22 | 0 | 154 |
|  | 6.2 | 5 | 4/4 | 15, 16, 24, 45 | −0.4 | 200 (1/4) |
| MMC | 3.0 | 1 | 4/4 | 16, 16, 18, 19 | −0.1 | 148 |
|  | 3.0 | 1 | 5/5 | 18, 21, 22, 40, 40 | 0 | 226 |
|  | 1.0 | 1 | 5/5 | 14, 15, 15, 16, 16 | −0.1 | 122 |
|  | 0.3 | 1 | 5/5 | 13, 13, 14, 14, 23 | −0.4 | 123 |
| ADM | 1.0 | 1 | 4/4 | 14, 16, 18, 29 | −0.6 | 154 |
|  | 0.3 | 1 | 4/4 | 15, 15, 16, 18 | −0.1 | 126 |

We claim:
1. A bis-acyloxymethyl having the structure:

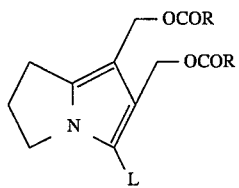

wherein L is selected from:

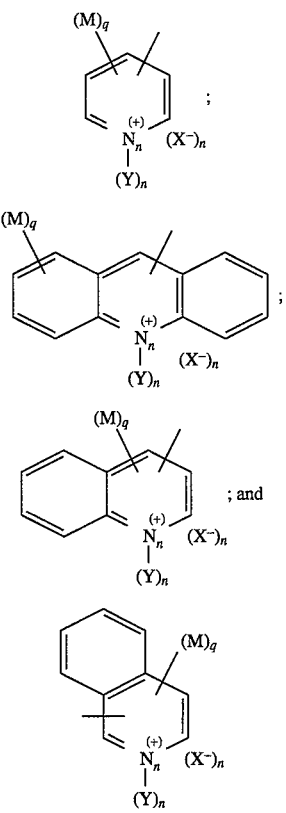

wherein Y is selected from hydrogen or

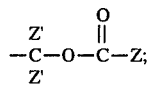

each R and Z is independently selected from hydrogen or substituted and unsubstituted alkyl, cycloalkyl, aryl, alkenyl, cycloalkenyl, alkynyl, and amine group of up to about 20 carbon atoms; each Z' is independently selected from hydrogen and substituted or unsubstituted alkyl of up to about 20 carbon atoms; M is Z or is selected from halogen, nitro, hydroxyl, nitrile and substituted or unsubstituted carboxylic acid group, carboxylic acid ester group, carboxylic acid amide group, sulfonic acid group, sulfonic acid amide group, ether group, thioether group, acylated hydroxyl, sulfonylamide, sulfonylurea, sulfoxide group and sulfone group containing up to about 20 carbon atoms; each n is the same and is 0 or 1; q is from 0–4; and, X is the anion of an acid.

2. A compound of claim 1 wherein R is selection from amine, aminoalkyl, aminocycloalkyl, aminoalkenyl, aminocycloalkenyl, and aminoaryl.

3. A compound of claim 1 wherein each Z' is hydrogen.
4. A compound of claim 1 wherein each M is hydrogen.
5. A compound of claim 1 wherein Z is selected from alkyl and aryl.
6. A compound of claim 5 wherein Z is selected from alkyl of 1–12 carbon atoms.
7. A compound of claim 6 wherein Z is selected from methyl, ethyl, propyl and butyl.
8. A compound of claim 5 wherein Z is phenyl.
9. A compound of claim 2 wherein each R is an alkylamine.
10. A compound of claim 9 wherein each R is isopropyl amine.
11. The chlorine, bromine, iodine, citrate, tartrate and acetate salt of a compound of claim 1.
12. A compound of claim 1 wherein n is 0.
13. A compound of claim 1 wherein each R is selected from aminoalkyl, aminoalkenyl and aminoaryl; each M and Z' are hydrogen; and n is 1.
14. A compound of claim 1 selected from the group consisting of 2,3-dihydro-5-(4-pyridinyl)-6,7-bis(hydroxymethyl)-1H-pyrrolizine Bis[N-(2-propyl)carbamate] ;2,3-dihydro-5-[4-(2-fluoropyridinyl)]-6,7-bis(hydroxymethyl-1H-pyrrolizine Bis[N-(2-propyl)carbamate]; 2,3-dihydro-5-[4-(2-chloropyridinyl)]-6,7-bis (hydroxymethyl-1H-pyrrolizine Bis[N-(2-propyl)carbamate]; 2,3-dihydro-5-[4-(2,6dichloropyridinyl)]-6,7-bis (hydroxymethyl-1H-pyrrolizine Bis[N-(2-propyl)carbamate]; 2,3-dihydro-5-(3-pyridinyl)-6,7-bis(hydroxymethyl)-1H-pyrrolizine Bis[N-(2-propyl)carbamate]; 2,3-dihydro-5-[5-(2-fluoropyridinyl)] -6,7-bis(hydroxymethyl)-1H-pyrrolizine Bis[N-(2-propyl)carbamate]; 2,3-dihydro-5-[5-(2-fluoropyridinyl)]-6,7-bis(hydroxymethyl)-1H-pyrrolizine Bis[N-(2-propyl)carbamate]; and 2,3-dihydro-5-[5-(2-chloropyridinyl)]-6,7-bis(hydroxymethyl)-1H-pyrrolizine Bis[N-(2-propyl)carbamate].
15. A compound of claim 1 selected from the group consisting of 1-[(propionyloxy)methyl]-4-{5-[2,3-dihydro-6,7-bis(n-(2-propyl)carbamoyloxymethyl)-1H-pyrrolizinyl]} Pyridinium iodide; 1-[(benzoyloxy)methyl]-4-{5-[2,3-dihydro-6,7-bis(N-(2-propyl)carbamoyloxymethyl)-1H-pyrrolizinyl]}pyridinium iodide; 1-[(propionyloxy)methyl]-3-{5-[2,3-dihydro-6,7-bis(N-(2-propyl)carbamoyloxymethyl)-1H-pyrrolizinyl]}pyridinium iodide; 1-[(benzoyloxy)methyl]-3-{5-[2,3-dihydro-6,7-bis(N-(2-propyl)carbamoyloxymethyl)-1H-pyrrolizinyl]} pyridinium iodide; and 1-methyl-4-{5-[2,3-dihydro-6,7-bis(N-(2-propyl)carbamoyloxymethyl)-1H-pyrrolizinyl]} pyridinium iodide.
16. A pharmaceutical comprising a pharmaceutical diluent and a compound of claim 1.
17. A pharmaceutical composition of claim 16 wherein each R is selected from substituted and unsubstituted aminoalkyl, aminoalkenyl, and aminoaryl.
18. A pharmaceutical composition of claim 16 wherein M is selected from hydrogen, alkyl, halogen and alkoxy.
19. A pharmaceutical composition of claim 16 wherein Z is selected from alkyl and aryl.
20. A pharmaceutical composition of claim 16 comprising an acid salt of at least one of said compounds.
21. A pharmaceutical composition of claim 16 wherein Z is selected from alkyl and alkoxy.
22. A pharmaceutical composition comprising a compound of claim 14.
23. A pharmaceutical composition comprising a compound of claim 15.

* * * * *